United States Patent
Brenner et al.

(10) Patent No.: US 6,492,407 B2
(45) Date of Patent: Dec. 10, 2002

(54) PHARMACEUTICAL COMPOSITIONS CONTAINING TRIAZOLONES AND METHODS OF TREATING NEURODEGENERATIVE DISEASE USING TRIAZOLONES

(75) Inventors: Michael Brenner, Bingen am Rhein (DE); Wolf-Dietrich Bechtel, Appenheim (DE); Rainer Palluk, Bingen am Rhein (DE); Marion Wienrich, Weiterstadt (DE); Thomas Weiser, Nieder-Olm (DE)

(73) Assignee: Boehringer Imgelheim Pharma KG, Ingelheim (DE)

( * ) Notice: Subject to any disclaimer, the term of this patent is extended or adjusted under 35 U.S.C. 154(b) by 0 days.

(21) Appl. No.: 09/840,281

(22) Filed: Apr. 23, 2001

(65) Prior Publication Data

US 2002/0045651 A1 Apr. 18, 2002

Related U.S. Application Data

(63) Continuation of application No. 09/291,493, filed on Apr. 14, 1999, now abandoned.

(30) Foreign Application Priority Data

Apr. 17, 1998 (DE) .......................... 198 16 882

(51) Int. Cl.$^7$ ............................... A61K 31/41
(52) U.S. Cl. ...................................... 514/384
(58) Field of Search .......................... 514/384

(56) References Cited

FOREIGN PATENT DOCUMENTS

GB          1311651        *  3/1973
WO          WO 94/11357    *  5/1994

* cited by examiner

Primary Examiner—Russell Travers
Assistant Examiner—Mojdeh Bahar
(74) Attorney, Agent, or Firm—Robert P. Raymond; Timothy X. Witkowski; Alan R. Stempel

(57) ABSTRACT

A method for treating a neurodegenerative disease or cerebral ischemia arising from conditions selected from the group consisting of Status epilepticus, hypoglycaemia, hypoxia, anoxia, brain trauma, brain oedema, amyotropic lateral sclerosis, Huntington's disease, Alzheimer's disease, hypotonia, cardiac infarction, brain pressure (elevated intracranial pressure), ischaemic and haemorrhagic stroke, global cerebral ischaemia with heart stoppage, diabetic polyneuropathy, tinnitus, perinatal asphyxia, psychosis, schizophrenia, depression, and Parkinson's disease, the method of treatment comprising administering to a host in need of such treatment a therapeutic amount of a compound of formula (I)

(I)

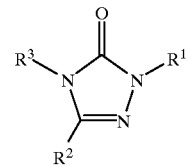

wherein $R^1$, $R^2$, $R^3$, $R^4$, $R^5$, $R^6$, and $R^7$ are as defined herein, or a pharmaceutically acceptable salt thereof, and pharmaceutical compositions containing a compound of formula (I).

4 Claims, No Drawings

PHARMACEUTICAL COMPOSITIONS CONTAINING TRIAZOLONES AND METHODS OF TREATING NEURODEGENERATIVE DISEASE USING TRIAZOLONES

This application is a continuation of USSN 09/291,493 filed Apr. 4, 1999, now abandoned.

The invention relates to the use of triazolones as pharmaceutical compositions, particularly pharmaceutical compositions with a neuroprotective activity, as well as new triazolones and processes for preparing them.

Triazolones are known from the prior art and are disclosed, for example, by published German applications DE 19521162 and DE 3631511 and also by European Patent applications EP 270 061 and EP 208 321. The compounds disclosed therein are effective pesticides and may be used in particular as insecticides and acaricides.

The present invention, by contrast, discloses triazolones which can be used as pharmaceuticals, particularly pharmaceutical compositions with a neuroprotective activity. Surprisingly, it has been found that the compounds according to the invention have an affinity for or an effect on various types of receptors and exhibit a neuroprotective activity.

Tests in vitro and in vivo have shown that the cell damage and loss of function occurring in the brain as a result of hypoglycaemia, hypoxia, anoxia, global and focal ischaemia, cranial brain trauma, brain oedema, and intercranial pressure are due in some measure to an increased synaptic activity and hence increased release of transmitters. Apart from glutamate, histamine and serotonin are of particular importance as neurotransmitters. Moreover, the concentrations of calcium and sodium ions in particular are changed.

It is known that after systemic administration of glutamate neurones are destroyed in mouse brains (S. M. Rothman and T. W. Olney, Trends in Neurosciences 10 (1987) 299). This finding leads one to conclude, inter alia, that glutamate plays a part in neurodegenerative diseases (R. Schwarcz and B. Meldrum, The Lancet 11 (1985) 140). Moreover, substances such as for example quisqualic acid, cainic acid, ibotenic acid, glutamic acid, N-methyl-D-aspartic acid (NMDA) and α-amino-3-hydroxy-5-methyl-4-isooxazolpropionic acid (AMPA) are known as exogenous or endogenous neurotoxins.

Brain lesions which may be induced by such substances are comparable with those which occur in conjunction with epilepsy and other neurodegenerative disorders, e.g., Huntington's disease and Alzheimer's disease. Substances and ions which inhibit the activity of the glutamate receptor and the ion channel connected to this receptor, e.g., competitive and non-competitive antagonists of excitatory amino acids, protect brain cells from hypoxic or ischaemic damage. These findings show that the glutamate receptors play an important part in mediating ischaemic damage.

It has been found that, surprisingly, the triazolones according to the invention have an antagonistic effect on the AMPA receptor. Moreover, these compounds exhibit a high affinity for the following type of receptor: "Na+ channel site 2" binding site. In view of these findings the compounds according to the invention may be used to treat neurodegenerative disorders and cerebral ischaemia of various origins.

The invention relates to the use of triazolones of general formula (I) as pharmaceutical compositions, particularly as pharmaceutical compositions with a neuroprotective activity,

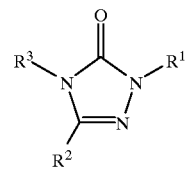

(I)

wherein:

$R^1$ denotes $C_6$–$C_{10}$-aryl, preferably phenyl, which may optionally be substituted directly or via a $C_1$–$C_4$-alkylene bridge by one or more of the groups halogen, nitro, —$CF_3$, —CN, —$OR^4$, —$COOR^4$, —$OCOR^4$, —$SR^5$, —$SO_2R^5$, —$OSO_2R^5$, —$NR^6R^7$, $C_1$–$C_4$-alkyl, $C_2$–$C_4$-alkenyl, or $C_2$–$C_4$-alkynyl;

$R^1$ denotes a $C_1$–$C_6$-alkyl, $C_2$–$C_6$-alkenyl or $C_2$–$C_6$-alkynyl group, which may optionally be substituted by phenyl, —$NR^6R^7$, halogen, nitro, —$CF_3$, —CN, or —$OR^4$;

$R^2$ denotes a $C_6$–$C_{10}$-aryl, preferably phenyl, which may optionally be substituted directly or via a $C_1$–$C_4$-alkylene bridge by one or more of the groups halogen, nitro, —$CF_3$, —CN, —$OR^4$, —$COOR^4$, —$OCOR^4$, —$SR^5$, —$SO_2R^5$, —$OSO_2R^5$, —$NR^6R^7$, $C_1$–$C_4$-alkyl, $C_2$–$C_4$-alkenyl, or $C_2$–$C_4$-alkynyl;

$R^2$ denotes a $C_1$–$C_6$-alkyl, $C_2$–$C_6$-alkenyl, or $C_2$–$C_6$-alkynyl group, which may optionally be substituted by phenyl, —$NR^6R^7$, halogen, nitro, —$CF_3$, —CN, or —$OR^4$;

$R^2$ denotes a C-linked 5- or 6-membered saturated or unsaturated heterocycle, which may contain as heteroatoms 1, 2, 3, or 4 atoms selected from the group comprising oxygen, nitrogen, or sulfur and which may optionally be substituted by $C_1$–$C_6$-alkyl or benzyl;

$R^3$ denotes hydrogen or a $C_1$–$C_6$-alkyl, $C_2$–$C_6$-alkenyl, or $C_2$–$C_6$-alkynyl group, which may optionally be substituted by —$NR^6R^7$, halogen, nitro, —$CF_3$, —CN, or —$OR^4$;

$R^4$ denotes hydrogen, $C_1$–$C_4$-alkyl optionally substituted by halogen or —$NR^6R^7$, or a phenyl or benzyl group, which may optionally carry one or more methoxy groups;

$R^5$ denotes hydrogen, $C_1$–$C_4$-alkyl, phenyl, or benzyl, wherein the phenyl or benzyl group may optionally be mono- or polysubstituted by methoxy;

$R^6$ denotes hydrogen, $C_3$–$C_6$-cycloalkyl, $C_1$–$C_6$-alkyl, $C_2$–$C_6$-alkenyl, or $C_2$–$C_6$-alkynyl, each of which may be mono- or polysubstituted by phenyl, benzyl, or —$OR^4$;

$R^6$ denotes $C_6$–$C_{10}$-aryl, preferably phenyl, or benzyl, which may optionally be substituted by halogen, —$OR^4$, $C_1$–$C_4$-alkyl, preferably —$CH_3$, —$SO_3H$, or —$COOR^4$;

$R^7$ denotes hydrogen, $C_3$–$C_6$-cycloalkyl, $C_1$–$C_6$-alkyl, $C_2$–$C_6$-alkenyl, or $C_2$–$C_6$-alkynyl, each of which may be mono- or polysubstituted by phenyl, benzyl, or —$OR^4$;

$R^7$ denotes $C_6$–$C_{10}$-aryl, preferably phenyl, or benzyl, which may optionally be substituted by halogen, —$OR^4$, $C_1$–$C_4$-alkyl, preferably —$CH_3$, —$SO_3H$, or —$COOR^4$; or $R^6$ and $R^7$ together with the nitrogen atom form a saturated or unsaturated 5- or 6-membered ring which may contain nitrogen, oxygen, or sulfur as further heteroatoms, whilst the heterocycle may be substituted by branched or unbranched alkyl group having 1 to 4 carbon atoms, may be substituted by phenyl or benzyl.

It is preferable to use compounds of general formula (I) as pharmaceutical compositions, particularly as pharmaceutical compositions with a neuroprotective activity, wherein $R^1$ denotes phenyl, which may optionally be substituted directly or via a $C_1$–$C_4$-alkylene bridge by one or more of the groups fluorine, chlorine, bromine, nitro, —$CF_3$, —CN, —$OR^4$, —$COOR^4$, —$OCOR^4$, —$NR^6R^7$, $C_1$–$C_4$-alkyl, $C_2$–$C_4$-alkenyl, or $C_2$–$C_4$-alkynyl;

$R^1$ denotes $C_1$–$C_4$-alkyl, which may optionally be substituted by phenyl;

$R^2$ denotes phenyl, which may optionally be substituted directly or via a $C_1$–$C_4$-alkylene bridge by one or more of the groups fluorine, chlorine, bromine, nitro, —$CF_3$, —CN, —$OR^4$, —$COOR^4$, —$OCOR^4$, —$NR^6R^7$, $C_1$–$C_4$-alkyl, $C_2$–$C_4$-alkynyl, or $C_2$–$C_4$-alkynyl;

$R^2$ denotes $C_1$–$C_4$-alkyl, which may optionally be substituted by phenyl;

$R^2$ denotes a C-linked 5- or 6-membered saturated or unsaturated heterocycle, which may contain as heteroatoms 1, 2, 3, or 4 atoms selected from the group comprising oxygen or nitrogen and which may optionally be substituted by $C_1$–$C_4$-alkyl or benzyl;

$R^3$ denotes hydrogen or a $C_1$–$C_4$-alkyl group, which may optionally be substituted by —$NR^6R^7$, fluorine, chlorine, bromine, nitro, —$CF_3$, —CN, or —$OR^4$;

$R^4$ denotes hydrogen, $C_1$–$C_4$-alkyl optionally substituted by halogen or —$NR^6R^7$, or a phenyl or benzyl group, which may optionally carry one or more methoxy groups;

$R^6$ denotes hydrogen, $C_1$–$C_4$-alkyl, $C_2$–$C_4$-alkenyl, or $C_2$–$C_4$-alkynyl, each of which may be mono- or polysubstituted by phenyl, benzyl, or —$OR^4$, $R^6$ denotes phenyl or benzyl, which may optionally be substituted by halogen, $OR^4$, $C_1$–$C_4$-alkyl, preferably —$CH_3$, —$SO_3H$, or —$COOR^4$;

$R^7$ denotes hydrogen, $C_1$–$C_4$-alkyl, $C_2$–$C_4$-alkenyl, or $C_2$–$C_4$-alkynyl, each of which may be mono- or polysubstituted by phenyl, benzyl, or —$OR^4$, $R^7$ denotes phenyl or benzyl, which may optionally be substituted by halogen, $OR^4$, $C_1$–$C_4$-alkyl, preferably —$CH_3$, —$SO_3H$, or —$COOR^4$; or $R^6$ and $R^7$ together with the nitrogen atom form a saturated or unsaturated 5- or 6-membered ring, which may contain nitrogen or oxygen as further heteroatoms, whilst the heterocycle may be substituted by a branched or unbranched alkyl group having 1 to 4 carbon atoms, or by phenyl or benzyl.

It is particularly preferred to use compounds of general formula (I) as pharmaceutical compositions, particularly as pharmaceutical compositions with a neuroprotective activity, wherein:

$R^1$ denotes phenyl which may optionally be substituted by one or more of the groups fluorine, chlorine, bromine, —$OR^4$, or $C_1$–$C_4$-alkyl;

$R^1$ denotes $C_1$–$C_4$-alkyl, which may optionally be substituted by phenyl;

$R^2$ denotes $C_1$–$C_4$-alkyl or phenyl which may optionally be substituted by one or more of the groups fluorine, chlorine, bromine, —$OR^4$, or $C_1$–$C_4$-alkyl;

$R^2$ denotes a C-linked 5- or 6-membered heterocycle selected from the group comprising furan, pyran, pyrrole, pyrazole, imidazole, triazole, tetrazole, pyridine, pyridazine, pyrimidine, pyrazine, triazine, oxazole, or isoxazole;

$R^3$ denotes hydrogen or a $C_1$–$C_4$-alkyl group, which may optionally be substituted by —$NR^6R^7$, chlorine, bromine, or —OH;

$R^4$ denotes hydrogen, $C_1$–$C_4$-alkyl optionally substituted by chlorine, bromine, or —$NR^6R^7$, or a phenyl or benzyl group;

$R^6$ denotes hydrogen, $C_1$–$C_4$-alkyl, phenyl, or benzyl;

$R^7$ denotes hydrogen, $C_1$–$C_4$-alkyl, phenyl, or benzyl; or $R^6$ and $R^7$ together with the nitrogen atom form a saturated or unsaturated 5- or 6-membered ring optionally substituted by $C_1$–$C_4$-alkyl or benzyl, selected from the group comprising piperidine, piperazine, morpholine, pyrrole, or pyrrolidine.

It is particularly preferable to use compounds of general formula (I) as pharmaceutical compositions, particularly as pharmaceutical compositions with a neuroprotective activity, wherein:

$R^1$ denotes methyl, ethyl, propyl, butyl, benzyl, or phenyl, which may optionally be substituted by one or more of the groups fluorine, chlorine, bromine, methyl, ethyl, propyl, or —$OR^4$;

$R^2$ denotes methyl, ethyl, propyl, butyl, or phenyl, which may optionally be substituted by one or more of the groups fluorine, chlorine, bromine, methyl, ethyl, propyl, or —$OR^4$;

$R^2$ denotes a C-linked heterocycle selected from pyrrole, pyrazole, imidazole, triazole, pyridine, pyridazine, pyrimidine, pyrazine, or triazine;

$R^3$ denotes hydrogen, methyl, ethyl, or propyl which may optionally be substituted by —$NR^6R^7$, chlorine, bromine, or —OH;

$R^4$ denotes hydrogen, methyl, ethyl, or propyl, which may optionally be substituted by —$NR^6R^7$, chlorine, bromine, or —OH;

$R^6$ denotes hydrogen, methyl ethyl, propyl, or benzyl;

$R^7$ denotes hydrogen, methyl ethyl, propyl, or benzyl; or $R^6$ and $R^7$ together with the nitrogen atom form a ring optionally substituted by methyl, ethyl, propyl, or benzyl, selected from the group comprising piperidine, piperazine, morpholine, pyrrole, or pyrrolidine.

Of particular interest according to the invention is the use of compounds of general formula (I) as pharmaceutical compositions, particularly as pharmaceutical compositions with a neuroprotective activity, wherein:

$R^1$ denotes methyl, ethyl, propyl, butyl, benzyl, or phenyl, which may optionally be substituted by one or more of the groups fluorine, chlorine, bromine, methyl, ethyl, propyl, or —$OR^4$;

$R^2$ denotes methyl, ethyl, propyl, butyl, or phenyl, which may optionally be substituted by one or more of the groups fluorine, chlorine, bromine, methyl, ethyl, propyl, or —$OR^4$;

$R^2$ denotes pyrrole, pyrazole, imidazole, pyridine, pyridazine, pyrimidine, or pyrazine;

$R^3$ denotes hydrogen, methyl, ethyl, or propyl, which may optionally be substituted by —$NR^6R^7$;

$R^4$ denotes methyl, ethyl, propyl, —$CH_2CH_2$—$NR^6R^7$, or —$CH_2CH_2CH_2$—$NR^6R^7$;

$R^6$ denotes hydrogen, methyl, ethyl, propyl, or benzyl; and $R^7$ denotes hydrogen, methyl, ethyl, propyl, or benzyl.

It is also particularly valuable to use compounds of general formula (I) as pharmaceutical compositions, particularly as pharmaceutical compositions with a neuroprotective activity, wherein:

$R^1$ denotes methyl, butyl, benzyl, or phenyl, which may optionally be substituted by one or more of the groups fluorine, chlorine, bromine, methyl, ethyl, or —$OR^4$;

$R^2$ denotes methyl, phenyl, which may optionally be substituted by one or more of the groups chlorine, methyl, or —$OR^4$;

$R^3$ denotes hydrogen, methyl, —$CH_2CH_2$—$NR^6R^7$, or —$CH_2CH_2CH_2$—$NR^6R^7$;

$R^4$ denotes methyl or —$CH_2CH_2$—$NR^6R^7$;

$R^6$ denotes methyl; and $R^7$ denotes methyl.

The invention also relates to pharmaceutical compositions, particularly pharmaceutical compositions with a neuroprotective activity containing as active substance one or more compounds of general formula (I), wherein the groups $R^1$, $R^2$, and $R^3$ are as hereinbefore defined.

The use of the compounds of general formula (I) includes the use of any enantiomers or diastereomers in optically pure form or in the form of mixtures which may be present. Furthermore the compounds of general formula (I) may be converted into their salts, particularly for pharmaceutical use into the physiologically acceptable salts with an inorganic or organic acid. Suitable acids include, for example, hydrochloric acid, hydrobromic acid, sulfuric acid, phosphoric acid, acetic acid, fumaric acid, succinic acid, lactic acid, methanesulfonic acid, citric acid, tartaric acid, or maleic acid. Mixtures of the abovementioned acids may also be used.

The activity of the compounds of general formula (I) at the AMPA receptor was demonstrated by electrophysiology on neuronal cells using methods known from the literature (patch-clamp method) (M. L. Mayer, L. Vyklicky, and G. L. Westbrook, J. Physiol. 415 (1989) 329 –350). The affinity of the triazolones of general formula (I) to the "$Na^+$ channel site 2" binding site was demonstrated as described by G. B. Brown (J. Neurosci. 6 (1986) 2064).

Apart from the use of the compounds of general formula (I) described above as pharmaceutical compositions, particularly as pharmaceutical compositions with a neuroprotective activity, the present invention is also directed to the new triazolones of general formula (I)

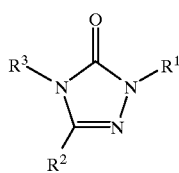

(I)

wherein:

$R^1$ denotes methyl, butyl, benzyl, or phenyl, which may optionally be substituted by one or more of the groups fluorine, chlorine, bromine, methyl, ethyl, or —$OR^4$;

$R^2$ denotes methyl, phenyl, which may optionally be substituted by one or more of the groups chlorine, methyl, or —$OR^4$;

$R^3$ denotes hydrogen, methyl, —$CH_2CH_2$—$NR^6R^7$, or —$CH_2CH_2CH_2$—$NR^6R^7$;

$R^4$ denotes methyl or —$CH_2CH_2$—$NR^6R^7$;

$R^6$ denotes methyl; and $R^7$ denotes methyl, with the proviso that $R^2$ cannot be 2-chlorophenyl and with the proviso that if a) $R^1$ denotes phenyl and $R^3$ denotes hydrogen, $R^2$ cannot denote phenyl, 4-chlorophenyl, 4-methylphenyl, or 4-methoxyphenyl;

b) $R^2$ denotes phenyl and $R^3$ denotes hydrogen, $R^1$ cannot denote phenyl, 4-chlorophenyl, 4-bromophenyl, 2,4-dibromophenyl, 4-methylphenyl, or 4-methoxyphenyl;

c) $R^3$ denotes methyl, $R^1$ and $R^2$ cannot simultaneously be phenyl, optionally in the form of their racemates, their enantiomers, in the form of their diastereomers and mixtures thereof, and optionally the pharmacologically acceptable acid addition salts thereof.

According to the invention, the preferred compounds are the compounds of general formula (I) wherein:

$R^1$ denotes phenyl, which may optionally be substituted by one or more of the groups fluorine, chlorine, bromine, methyl, ethyl, or methoxy;

$R^2$ denotes phenyl, which may optionally be substituted by methoxy; and $R^3$ denotes hydrogen, methyl, or —$CH_2CH_2$—$NMe_2$;

with the proviso that if a) $R^1$ denotes phenyl and $R^3$ denotes hydrogen, $R^2$ cannot denote phenyl or 4-methoxyphenyl;

b) $R^2$ denotes phenyl and $R^3$ denotes hydrogen, $R^1$ cannot denote phenyl, 4-chlorophenyl, 4-bromophenyl, 2,4-dibromophenyl, 4-methylphenyl, or 4-methoxyphenyl;

c) $R^3$ denotes methyl, $R^1$ and $R^2$ cannot simultaneously be phenyl, optionally in the form of their racemates, their enantiomers, in the form of their diastereomers and mixtures thereof, and optionally the pharmacologically acceptable acid addition salts thereof.

The following compounds are particularly preferred according to the invention:

2-(2-methylphenyl)-5-phenyl-3H-1,2,4-triazol-3-one;

2-(3-methoxyphenyl)-4-methyl-5-phenyl-3H-1,2,4-triazol-3-one;

2-(2-bromophenyl)-4-methyl-5-phenyl-3H-1,2,4-triazol-3-one;

5-(4-methoxyphenyl)-4-methyl-2-phenyl-3H-1,2,4-triazol-3-one;

5-(2-methoxyphenyl)-4-methyl-2-phenyl-3H-1,2,4-triazol-3-one;

4-(2-N,N-dimethylaminoethyl)-2-(2-methylphenyl)-5-phenyl-3H-1,2,4-triazol-3-one;

2-(2-methoxyphenyl)-5-phenyl-3H-1,2,4-triazol-3-one;

2-(2-chlorophenyl)-5-phenyl-3H-1,2,4-triazol-3-one;

2-(3-chlorophenyl)-4-(2-N,N-dimethylaminoethyl)-5-phenyl-3H-1,2,4-triazol-3-one;

2-(2-fluorophenyl)-5-phenyl-3H-1,2,4-triazol-3-one;

2-(3-fluorophenyl)-4-methyl-5-phenyl-3H-1,2,4-triazol-3-one;

2-(2-fluorophenyl)-4-methyl-5-phenyl-3H -1,2,4-triazol-3-one; 2-(3-methylphenyl)-5-phenyl-3H-1,2,4-triazol-3-one;

2-(2-ethylphenyl)-5-phenyl-3H-1,2,4-triazol-3-one;

2-(3-fluorophenyl)-4-(2-N,N-dimethylaminoethyl)-5-phenyl-3H-1,2,4-triazol-3-one;

4-methyl-2-(3-methylphenyl)-5-phenyl-3H-1,2,4-triazol-3-one;

4-(2-N,N-dimethylaminoethyl)-2-(3-methylphenyl)-5-phenyl-3H-1,2,4-triazol-3-one; 2-(2-chlorophenyl)-4-methyl-5-phenyl-3H-1,2,4-triazol-3-one; and 2-(2-bromophenyl)-5-phenyl-3H-1,2,4-triazol-3-one.

The compounds of general formula (I) optionally obtained in the form of their racemates, enantiomers, diastereomers and mixtures thereof may be converted into the salts thereof, particularly for pharmaceutical use, into the physiologically acceptable salts thereof with an inorganic or organic acid. Acids suitable for this purpose include, for example, hydrochloric acid, hydrobromic acid, sulfuric acid, phosphoric acid, methanesulfonic acid, acetic acid, fumaric acid, succinic acid, lactic acid, citric acid, tartaric acid, or maleic acid. Mixtures of the abovementioned acids may also be used.

The term alkyl groups (including those which are components of other groups, e.g., alkylene bridges), unless otherwise stated, denotes branched and unbranched alkyl groups having 1 to 6 carbon atoms, preferably 1 to 4 carbon atoms. Examples include: methyl, ethyl, n-propyl, isopropyl, butyl, isobutyl, sec-butyl, tert-butyl, pentyl, isopentyl, hexyl, heptyl and octyl. The groups methyl, ethyl, butyl, or tert-butyl are also referred to by the abbreviations Me, Et, Bu, or tBu.

Unless otherwise specified, substituted alkyl groups (including those which are components of other groups) may carry one or more of the following substituents, for example: halogen, hydroxy, mercapto, $C_1$–$C_6$-alkyloxy, amino, alkylamino, dialkylamino, cyano, nitro, =O, —CHO, —COOH, —COO—$C_1$–$C_6$-alkyl, or —S—$C_1$–$C_6$-alkyl.

Examples of alkenyl groups (including those which are part of other groups) include branched and unbranched alkenyl groups having 2 to 6 carbon atoms, preferably 2 to 3 carbon atoms, if they have at least one double bond, e.g., the alkyl groups mentioned above if they have at least one double bond, such as vinyl (provided that no unstable enamines or enol-ethers are formed), propenyl, isopropenyl, butenyl, pentenyl and hexenyl.

Unless otherwise specified, substituted alkenyl groups (including those which are part of other groups) may for example carry one or more of the following substituents: halogen, hydroxy, mercapto, $C_1$–$C_6$-alkyloxy, amino, alkylamino, dialkylamino, cyano, nitro, =O, —CHO, —COOH, —COO—$C_1$–$C_6$-alkyl, or —S—$C_1$–$C_6$-alkyl.

Examples of alkynyl groups (including those which are part of other groups) are alkynyl groups having 2 to 10 carbon atoms provided that they have at least one triple bond, such as ethynyl, propargyl, butynyl, pentynyl and hexynyl.

Unless otherwise specified, substituted alkynyl groups (including those which are part of other groups) may, for example, carry one or more of the following substituents: halogen, hydroxy, mercapto, $C_1$–$C_6$-alkyloxy, amino, alkylamino, dialkylamino, cyano, nitro, =O, —CHO, —COOH, —COO—$C_1$–$C_6$-alkyl, —S—$C_1$–$C_6$-alkyl.

Examples of cycloalkyl groups having 3 to 6 carbon atoms include cyclopropyl, cyclobutyl, cyclopentyl, or cyclohexyl, which may also be substituted by branched or unbranched $C_1$–$C_4$-alkyl, hydroxy and/or halogen, or may be substituted as hereinbefore. The term halogen generally refers to fluorine, chlorine, bromine, or iodine.

The term aryl denotes an aromatic ring system having 6 to 10 carbon atoms which, unless otherwise specified, may for example carry one or more of the following substituents: $C_1$–$C_6$-alkyl, $C_1$–$C_6$-alkyloxy, halogen, hydroxy, mercapto, amino, alkylamino, dialkylamino, —$CF_3$, cyano, nitro, —CHO, —COOH, —COO—$C_1$–$C_6$-alkyl, —S—$C_1$–$C_6$-alkyl. The preferred aryl group is phenyl.

Examples of N-linked cyclic groups of general formula $NR^5R^6$ include: pyrrole, pyrroline, pyrrolidine, 2-methylpyrrolidine, 3-methylpyrrolidine, piperidine, piperazine, N-methylpiperazine, N-ethylpiperazine, N-(n-propyl)piperazine, N-benzylpiperazine, morpholine, thiomorpholine, imidazole, imidazoline, imidazolidine, pyrazole, pyrazoline, pyrazolidine, preferably morpholine, N-benzylpiperazine, piperazine and piperidine, whilst the above-mentioned heterocycles may be substituted by $C_1$–$C_4$-alkyl, preferably methyl.

Examples of C-linked 5- or 6-membered heterocyclic rings which may contain nitrogen, oxygen or sulfur as heteroatoms, include furan, tetrahydrofuran, 2-methyltetrahydrofuran, 2-hydroxymethylfuran, tetrahydrofuranone, γ-butyrolactone, α-pyran, γ-pyran, dioxolane, tetrahydropyran, dioxane, thiophene, dihydrothiophene, thiolane, dithiolane, pyrrole, pyrroline, pyrrolidine, pyrazole, pyrazoline, imidazole, imidazoline, imidazolidine, triazole, tetrazole, pyridine, piperidine, pyridazine, pyrimidine, pyrazine, piperazine, triazine, tetrazine, morpholine, thiomorpholine, oxazole, isoxazole, oxazine, thiazole, isothiazole, thiadiazole, oxadiazole, pyrazolidine, whilst the heterocycle may be substituted as specified in the definitions.

"=O" denotes an oxygen atom linked via a double bond.

The compounds according to the invention may, for example, be synthesized by the method illustrated in Diagram 1.

Diagram 1

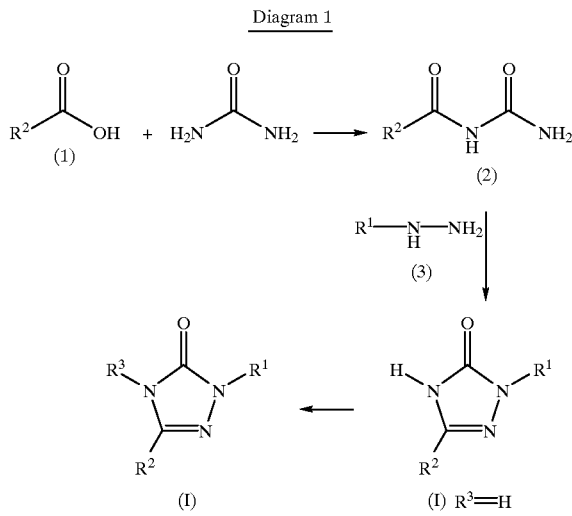

For this, the carboxylic acid derivatives (1) are converted with urea into the N-acylureas (2). From these the triazolones of general formula (I) wherein $R^3$ is hydrogen may be obtained by reacting with correspondingly substituted hydrazine derivatives (3), and these can be converted into the compounds of general formula (I) by alkylation under basic conditions. Suitable alkylating agents include chlorides, bromides, iodides, methanesulfonates, trifluoromethanesulfonates, or p-toluenesulfonates.

The present invention will now be explained more fully with reference to the following general synthesis instructions, without restricting it to their contents.

a) General instructions for preparing the N-acylureas (2):

0.1 mol of carboxylic acid derivative (1) is dissolved together with 0.1 mol of urea, 0.1 mol of triphenylphosphite, and 0.1 mol of pyridine in 100 ml DMF and stirred at 100° C. until the reaction has ended (5 to 24 hours). The DMF is evaporated in vacuo, the residue is added to water and recrystallized from ethanol. Yield: 15%–50%.

b) General method for preparing the triazolones (I, with R³=H):

0.01 mol of N-acylurea compound (2) is stirred with 0.01 mol of hydrazine derivative (3) in 30 ml of decaline at 170° C. for 1 to 6 hours. The mixture is left to cool and the crystals formed are filtered off, washed with diethylether, and recrystallized from ethyl acetate. Yield: 20%–70%.

c) General method for preparing the triazolones (I, with R³=methyl):

1.2 mmol of triazolone compound (I, with R³=H) is stirred with 2.4 mmol of methyl iodide and 2.4 mmol of potassium carbonate in 20 ml of acetone for 3 hours at 60° C. The acetone is evaporated in vacuo, the residue is taken up in water and ethyl acetate, and the aqueous phase is extracted twice with ethyl acetate. The combined ethyl acetate phases are dried over sodium sulfate and evaporated in vacuo. The product is purified by chromatography on silica gel with methylene chloride or toluene/methanol with subsequent recrystallization from isopropanol/petrol or ethanol. Yield: 45% to 70%.

d) General method for preparing the triazolones (I, with R³=2-dimethylaminoethyl):

1. 1.6 mmol of triazolone compound (I, with R³=H) is dissolved in DMF, stirred with 1.6 mmol of a 60% sodium hydride suspension in oil at 80° C. for 0.5 hours and then combined with 4.8 mmol of dibromoethane. The mixture is stirred for 4 hours at 120° C.

The DMF is evaporated in vacuo, the residue is taken up in water and ethyl acetate, and the aqueous phase is extracted once more with ethyl acetate. The combined ethyl acetate phases are dried over sodium sulfate and evaporated in vacuo. The product is purified by chromatography on silica gel with toluene/ethyl acetate mixtures. The quantity of bromoethane derivative thus obtained is reacted for 2 hours at 1.8 bar with an excess of dimethylamine at 100° C. in dioxane. The dioxane is evaporated in vacuo and the residue is taken up in dilute aqueous hydrochloric acid solution and ethyl acetate. The organic phase is extracted twice more with dilute aqueous hydrochloric acid solution and the combined extracts are made alkaline with ammonia solution. The ammoniacal solution is extracted 3 times with ethyl acetate and the combined organic phases are dried over sodium sulfate and evaporated in vacuo. The residue is taken up in ethanol, combined with ethereal HCl, and the hydrochloride is precipitated with anhydrous ether. Yield: 35%–50%.

The compounds of general formula (I) listed in Table 1 may be prepared by the methods described above or by analogous methods:

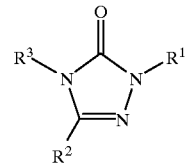

(I)

TABLE 1

| Ex. | -R¹ | -R² | -R³ | M.p. [° C.] | Chemical Name |
|---|---|---|---|---|---|
| 1 | 2-methylphenyl | phenyl | —H | 208–211 | 2-(2-methyl-phenyl)-5-phenyl-3H-1,2,4-triazol-3-one |
| 2 | 4-methoxyphenyl | phenyl | —H | 220–224 | 2-(4-methoxy-phenyl)-5-phenyl-3H-1,2,4-triazol-3-one |
| 3 | phenyl | phenyl | ∼∼NMe₂ | 220–226 | (4-(2-N,N-dimethyl-aminoethyl)-2,5-diphenyl-3H-1,2,4-triazol-3-one |
| 4 | 3-methoxyphenyl | phenyl | —H | 224–226 | 2-(3-methoxy-phenyl)-5-phenyl-3H-1,2,4-triazol-3-one |
| 5 | 3-methoxyphenyl | phenyl | -methyl | 81–83 | 2-(3-methoxy-phenyl)-4-methyl-5-phenyl-3H-1,2,4-triazol-3-one |
| 6 | 2-methylphenyl | phenyl | -methyl | 91–93 | 4-methyl-2-(2-methyl-phenyl)-5-phenyl-3H-1,2,4-triazol-3-one |

TABLE 1-continued

| Ex. | -R¹ | -R² | -R³ | M.p. [° C.] | Chemical Name |
|---|---|---|---|---|---|
| 7 | phenyl | 4-chlorophenyl | —H | — | 5-(4-chlorophenyl)-2-phenyl-3H-1,2,4-triazol-3-one |
| 8 | 2-bromophenyl | phenyl | -methyl | 80–82 | 2-(2-bromophenyl)-4-methyl-5-phenyl-3H-1,2,4-triazol-3-one |
| 9 | 2-bromophenyl | phenyl | —CH₂CH₂NMe₂ | 234–236[a] | 2-(2-bromophenyl)-4-(2-N,N-dimethylaminoethyl)-5-phenyl-3H-1,2,4-triazol-3-one |
| 10 | phenyl | 4-methoxyphenyl | —H | 233–235 | 5-(4-methoxyphenyl)-2-phenyl-3H-1,2,4-triazol-3-one |
| 11 | phenyl | 3,4-dichlorophenyl | —H | >300 | 5-(3,4-dichlorophenyl)-2-phenyl-3H-1,2,4-triazol-3-one |
| 12 | 3-methoxyphenyl | phenyl | —CH₂CH₂NMe₂ | 227–230[a] | 4-(2-N,N-dimethylaminoethyl)-2-(3-methoxyphenyl)-5-phenyl-3H-1,2,4-triazol-3-one |
| 13 | phenyl | 4-methylphenyl | —H | 255 | 5-(4-methylphenyl)-2-phenyl-3H-1,2,4-triazol-3-one |
| 14 | phenyl | phenyl | —CH₂CH₂CH₂NMe₂ | 72[a] | 4-(3-N,N-dimethylaminopropyl)-2,5-diphenyl-3H-1,2,4-triazol-3-one |
| 15 | 4-methylphenyl | phenyl | —H | 234–236 | 2-(4-methylphenyl)-5-phenyl-3H-1,2,4-triazol-3-one |
| 16 | 4-chlorophenyl | phenyl | —H | 258–268 | 2-(4-chlorophenyl)-5-phenyl-3H-1,2,4-triazol-3-one |
| 17 | phenyl | 4-methylphenyl | -methyl | 109–111 | 5-(4-methylphenyl)-4-methyl-2-phenyl-3H-1,2,4-triazol-3-one |
| 18 | 4-methylphenyl | phenyl | -methyl | 108 | 2-(4-methylphenyl)-4-methyl-5-phenyl-3H-1,2,4-triazol-3-one |
| 19 | phenyl | 3,4-dichlorophenyl | -methyl | 111–113 | 5-(3,4-dichlorophenyl)-4-methyl-2-phenyl-3H-1,2,4-triazol-3-one |

TABLE 1-continued

| Ex. | -R¹ | -R² | -R³ | M.p. [° C.] | Chemical Name |
|---|---|---|---|---|---|
| 20 | 4-Cl-phenyl | phenyl | -methyl | 110–111 | 2-(4-chloro-phenyl)-4-methyl-2-phenyl-3H-1,2,4-triazol-3-one |
| 21 | phenyl | 2-Me-phenyl | —H | 176 | 5-(2-methyl-phenyl)-2-phenyl-3H-1,2,4-triazol-3-one |
| 22 | phenyl | 4-OMe-phenyl | -methyl | 118 | 5-(4-methoxy-phenyl)-4-methyl-2-phenyl-3H-1,2,4-triazol-3-one |
| 23 | phenyl | 2-Me-phenyl | -methyl | 88–89 | 5-(2-methyl-phenyl)-4-methyl-2-phenyl-3H-1,2,4-triazol-3-one |
| 24 | phenyl | 2-MeO-phenyl | —H | 217 | 5-(2-methoxy-phenyl)-2-phenyl-3H-1,2,4-triazol-3-one |
| 25 | phenyl | 2-MeO-phenyl | -methyl | 117 | 5-(2-methoxy-phenyl)-4-methyl-2-phenyl-3H-1,2,4-triazol-3-one |
| 26 | 3,4-dichloro-phenyl | phenyl | —H | >280 | 2-(3,4-dichloro-phenyl)-5-phenyl-3H-1,2,4-triazol-3-one |
| 27 | 2-Me-phenyl | phenyl | -CH₂CH₂-NMe₂ | 204–207[a] | 4-(2-N,N-dimethyl-aminoethyl)-2-(2-methyl-phenyl)-5-phenyl-3H-1,2,4-triazol-3-one |
| 28 | 2,3-dimethyl-phenyl | phenyl | —H | 253 | 2-(2,5-dimethyl-phenyl)-5-phenyl-3H-1,2,4-triazol-3-one |
| 29 | phenyl | 2-Me-6-(OCH₂CH₂NMe)-phenyl | -methyl | 184–186[a] | 4-methyl-5-[2-(2-N,N-dimethylamino-ethyl)phenyl]-2-phenyl-3H-1,2,4-triazol-3-one |

TABLE 1-continued

| Ex. | -R¹ | -R² | -R³ | M.p. [° C.] | Chemical Name |
|---|---|---|---|---|---|
| 30 | 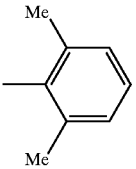 | 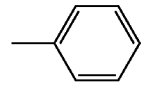 | -methyl | 101–103 | 4-methyl-2-(2,5-dimethyl-phenyl)-5-phenyl-3H-1,2,4-triazol-3-one |
| 31 | 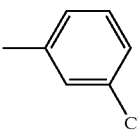 | 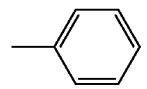 | —H | 264 | 2-(3-chloro-phenyl)-5-phenyl-3H-1,2,4-triazol-3-one |
| 32 | 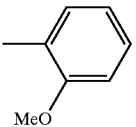 | 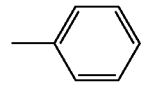 | —H | 275–277 | 2-(2-methoxy-phenyl)-5-phenyl-3H-1,2,4-triazol-3-one |
| 33 | 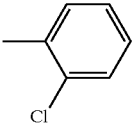 | 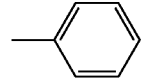 | —H | 257 | 2-(2-chloro-phenyl)-5-phenyl-3H-1,2,4-triazol-3-one |
| 34 | 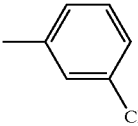 | 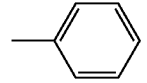 | -methyl | 82–83 | 2-(3-chloro-phenyl)-4-methyl-5-phenyl-3H-1,2,4-triazol-3-one |
| 35 | 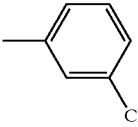 | 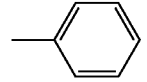 | 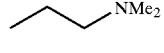 | 196[a] | 2-(3-chloro-phenyl)-4-(2-N,N-dimethylamino-ethyl)-5-phenyl-3H-1,2,4-triazol-3-one |
| 36 | 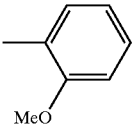 | 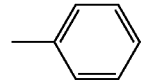 | -methyl | 105 | 2-(2-methoxy-phenyl)-4-methyl-5-phenyl-3H-1,2,4-triazol-3-one |
| 37 | 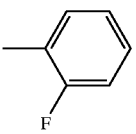 | 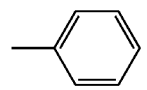 | —H | 238–240 | 2-(2-fluoro-phenyl)-5-phenyl-3H-1,2,4-triazol-3-one |
| 38 | 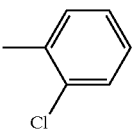 | 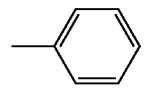 | 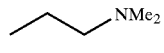 | 228–230[a] | 2-(2-chloro-phenyl)-4-(2-N,N-dimethylamino-ethyl)-5-phenyl-3H-1,2,4-triazol-3-one |
| 39 | 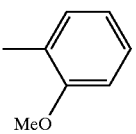 | 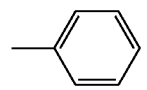 | 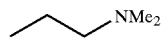 | 240–242[a] | 2-(2-methoxy-phenyl)-4-(2-N,N-dimethylamino-ethyl)-5-phenyl-3H-1,2,4-triazol-3-one |

TABLE 1-continued

| Ex. | -R¹ | -R² | -R³ | M.p. [° C.] | Chemical Name |
|---|---|---|---|---|---|
| 40 | 2-methyl-phenyl-O-CH₂CH₂-NMe (attached at position shown) | phenyl | -methyl | 188–191[a] | 4-methyl-2-[2-(2-N,N-dimethylamino-ethyl)phenyl]-5-phenyl-3H-1,2,4-triazol-3-one |
| 41 | 3-fluorophenyl | phenyl | —H | 253–254 | 2-(3-fluoro-phenyl)-5-phenyl-3H-1,2,4-triazol-3-one |
| 42 | 3-fluorophenyl | phenyl | -methyl | 81 | 2-(3-fluoro-phenyl)-4-methyl-5-phenyl-3H-1,2,4-triazol-3-one |
| 43 | 2-fluorophenyl | phenyl | -CH₂CH₂CH₂NMe₂ | 201–202[a] | 2-(2-fluoro-phenyl)-4-(2-N,N-dimethylamino-ethyl)-5-phenyl-3H-1,2,4-triazol-3-one |
| 44 | 2-fluorophenyl | phenyl | -methyl | 65–66 | 2-(2-fluoro-phenyl)-4-methyl-5-phenyl-3H-1,2,4-triazol-3-one |
| 45 | 2,5-dimethylphenyl | phenyl | -CH₂CH₂CH₂NMe₂ | 215–217[a] | 4-(2-N,N-dimethyl-amino-ethyl)-2-(2,5-dimethyl-phenyl)-5-phenyl-3H-1,2,4-triazol-3-one |
| 46 | 3-methylphenyl | phenyl | —H | 207–208[a] | 2-(3-methyl-phenyl)-5-phenyl-3H-1,2,4-triazol-3-one |
| 47 | 2,5-dichlorophenyl | phenyl | —H | 297 | 2-(2,5-dichloro-phenyl)-5-phenyl-3H-1,2,4-triazol-3-one |
| 48 | 2-ethylphenyl | phenyl | —H | 209–210 | 2-(2-ethyl-phenyl)-5-phenyl-3H-1,2,4-triazol-3-one |
| 49 | 4-fluorophenyl | phenyl | -CH₂CH₂CH₂NMe₂ | 201–203[a] | 2-(3-fluorophenyl)-4-(2-N,N-dimethyl-aminoethyl)-5-phenyl-3H-1,2,4-triazol-3-one |

TABLE 1-continued

| Ex. | -R¹ | -R² | -R³ | M.p. [° C.] | Chemical Name |
|---|---|---|---|---|---|
| 50 | 3-methylphenyl | phenyl | -methyl | 91–92 | 4-methyl-2-(3-methyl-phenyl)-5-phenyl-3H-1,2,4-triazol-3-one |
| 51 | 2,6-dichlorophenyl | phenyl | -methyl | 156–158 | 2-(2,5-dichloro-phenyl)-4-methyl-5-phenyl-3H-1,2,4-triazol-3-one |
| 52 | 2-(methylmethyl)phenyl | phenyl | -methyl | 72–74 | 2-(2-ethyl-phenyl)-4-methyl-5-phenyl-3H-1,2,4-triazol-3-one |
| 53 | 3-methylphenyl | phenyl | -CH₂CH₂NMe₂ | 204–206[a] | 4-(2-N,N-dimethyl-amino-ethyl)-2-(3-methyl-phenyl)-5-phenyl-3H-1,2,4-triazol-3-one |
| 54 | 2-(methylmethyl)phenyl | phenyl | -CH₂CH₂NMe₂ | 203[a] | 2-(2-ethylphenyl)-4-(2-N,N-dimethylamino-ethyl)-5-phenyl-3H-1,2,4-triazol-3-one |
| 55 | 2-chlorophenyl | phenyl | -methyl | 94–96 | 2-(2-chloro-phenyl)-4-methyl-5-phenyl-3H-1,2,4-triazol-3-one |
| 56 | 2-bromophenyl | phenyl | —H | 246–264 | 2-(2-bromo-phenyl)-5-phenyl-3H-1,2,4-triazol-3-one |
| 57 | 2,6-dichlorophenyl | phenyl | -CH₂CH₂NMe₂ | 222–224[a] | 2-(2,5-dichloro-phenyl)-4-(2-N,N-dimethylamino-ethyl)-5-phenyl-3H-1,2,4-triazol-3-one |
| 58 | phenyl | phenyl | -methyl | | 4-methyl-2,5-diphenyl-3H-1,2,4-triazol-3-one |
| 59 | phenyl | phenyl | —H | 234–237 | 2,5-Diphenyl-3H-1,2,4-triazol-3-one |
| 60 | benzyl | phenyl | —H | 220 | 2-benzyl-5-phenyl-3H-1,2,4-triazol-3-one |

TABLE 1-continued

| Ex. | -R¹ | -R² | -R³ | M.p. [° C.] | Chemical Name |
|---|---|---|---|---|---|
| 61 | 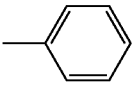 | -methyl | —H | 185–187 | 5-methyl-2-phenyl-3H-1,2,4-triazol-3-one |
| 62 | 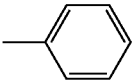 | -methyl | -methyl | 96–98 | 4,5-dimethyl-2-phenyl-3H-1,2,4-triazol-3-one |
| 63 | -methyl | 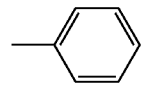 | —H | 217–218 | 2-methyl-5-phenyl-3H-1,2,4-triazol-3-one |
| 64 | 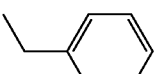 | 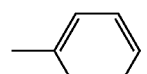 | -methyl | 62–64 | 2-benzyl-4-methyl-5-phenyl-3H-1,2,4-triazol-3-one |
| 65 | -tert-butyl | 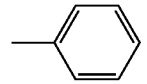 | —H | 171–173 | 2-tert-butyl-5-phenyl-3H-1,2,4-triazol-3-one |
| 66 | 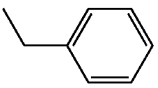 | 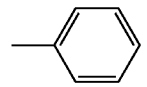 | 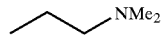 | 188–190[a] | 2-benzyl-4-(2-N,N-dimethylaminoethyl)-5-phenyl-3H-1,2,4-triazol-3-one |
| 67 | -methyl | 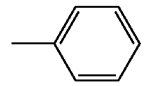 | -methyl | 140–142 | 2,4-dimethyl-5-phenyl-3H-1,2,4-triazol-3-one |
| 68 | -methyl | 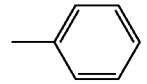 | 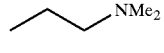 | 192–194[a] | 2-methyl-4-(2-N,N-dimethylaminoethyl)-5-phenyl-3H-1,2,4-triazol-3-one |
| 69 | -tert-butyl | 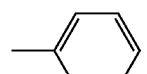 | -methyl | 67–68 | 2-tert-butyl-4-methyl-5-phenyl-3H-1,2,4-triazol-3-one |
| 70 | 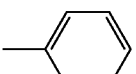 | -methyl | 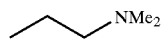 | 139[a] | 5-methyl-4-(2-N,N-dimethylaminoethyl)-2-phenyl-3H-1,2,4-triazol-3-one |
| 71 | -tert-butyl | 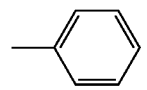 | 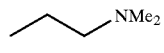 | 162[a] | 2-tert-butyl-4-(2-N,N-dimethylaminoethyl)-5-phenyl-3H-1,2,4-triazol-3-one |
| 72 | 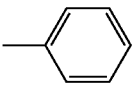 | 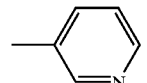 | 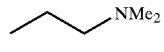 | 229[b] | 4-(2-N,N-dimethylaminoethyl)-2-phenyl-5-(3-pyridyl)-3H-1,2,4-triazol-3-one |
| 73 | 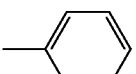 | 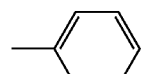 | —H | 246[a] | 2-phenyl-5-(3-pyridyl)-3H-1,2,4-triazol-3-one |
| 74 | 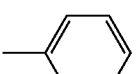 | 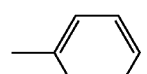 | -methyl | 185–187[a] | 4-methyl-2-phenyl-5-(3-pyridyl)-3H-1,2,4-triazol-3-one |

TABLE 1-continued

| Ex. | -R¹ | -R² | -R³ | M.p. [° C.] | Chemical Name |
|---|---|---|---|---|---|
| 75 | phenyl | 4-pyridyl | —H | 290 | 2-phenyl-5-(4-pyridyl)-3H-1,2,4-triazol-3-one |

Legend:
a: x HCl;
b: x 2HCl.

The activity at the AMPA receptor was demonstrated by electrophysiology on neuronal cells (patch-clamp method) (M. L. Mayer, L. Vyklicky, and G. L. Westbrook, J. Physiol. 415(1989) 329 –350). The testing was carried out at a test concentration of 100 μM.

TABLE 2

Inhibition of the cainate-induced signal at the AMPA receptor

| Example | AMPA Inh. [%] |
|---|---|
| 1 | 58 |
| 5 | 58 |
| 8 | 87 |
| 22 | 50 |
| 25 | 72 |
| 27 | 64 |
| 32 | 73 |
| 33 | 97 |
| 37 | 86 |
| 42 | 96 |
| 44 | 76 |
| 46 | 54 |
| 48 | 63 |
| 50 | 71 |
| 55 | 80 |
| 56 | 96 |

The affinity to the "Na⁺ channel site 2" binding site was demonstrated as described by G. B. Brown (J. Neurosci. 6 (1986) 2064). The testing was typically carried out at a test concentration of 10 μM and the results are presented in Table 3.

TABLE 3

| Example | Ki [μm] |
|---|---|
| 27 | 5.41 |
| 35 | 2.08 |
| 49 | 6.58 |
| 53 | 5.78 |

The results described above show that the triazolone derivatives of general formula (I) can be used in the treatment of neurodegenerative diseases and cerebral ischaemia of various origins. These include, for example, Status epilepticus, hypoglycaemia, hypoxia, anoxia, brain trauma, brain oedema, amyotropic lateral sclerosis, Huntington's disease, Alzheimer's disease, hypotonia, cardiac infarction, brain pressure (elevated intracranial pressure), ischaemic and haemorrhagic stroke, global cerebral ischaemia with heart stoppage, diabetic polyneuropathy, tinnitus, perinatal asphyxia, psychosis, schizophrenia, depression, and Parkinson's disease.

The compounds of general formula (I) may be used on their own or in conjunction with other active substances according to the invention, optionally also in conjunction with other pharmacologically active substances. Suitable preparations include for example tablets, capsules, suppositories, solutions, particularly solutions for injection (s.c., i.v., i.m.) and infusion, elixirs, emulsions, or dispersible powders. The content of the pharmaceutically active compound(s) should be in the range from 0.1 wt. % to 90 wt. %, preferably 0.5 to 50 wt.-% of the composition as a whole, i.e., in amounts which are sufficient to achieve the dosage range specified below.

Suitable tablets may be obtained, for example, by mixing the active substance(s) with known excipients, for example inert diluents such as calcium carbonate, calcium phosphate, or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidine or shellac, gum arabic, talc, titanium dioxide, or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol, or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g., with the addition of isotonic agents, preservatives such as p-hydroxybenzoates, or stabilizers such as alkali metal salts of ethylenediamine tetraacetic acid, optionally using emulsifiers and/or dispersants, whilst if water is used as the diluent, for example, optionally organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, chalk), synthetic mineral powders (e.g., highly dispersed silicic acid and silicates), sugars (e.g., cane sugar, lactose and glucose) emulsifiers (e.g., lignin, spent sulfite liquors, methylcellulose, starch and polyvinylpyrrolidone) and lubricants (e.g., magnesium stearate, talc, stearic acid and sodium lauryl sulfate).

The preparations are administered by the usual methods, preferably by parenteral route, particularly by intravenous infusion. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulfate and talc may be used at the same time for the tabletting process. In the case of aqueous suspensions the active substances may be combined with various flavor enhancers or colorings in addition to the excipients mentioned above.

For parenteral use, solutions of the active substances with suitable liquid carriers may be used.

The dosage for intravenous use is from 1 mg to 1000 mg per hour, preferably between 5 mg and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

Moreover, the compounds of general formula I or the acid addition salts thereof may also be combined with other types of active substance.

The Examples which follow illustrate the present invention without restricting its scope:

Examples of Pharmaceutical Formulations

| A. Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B. Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C. Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

What is claimed is:

1. A pharmaceutical composition comprising a compound selected from the group consisting of:
    (a) 2-(2-methylphenyl)-5-phenyl-3H-1,2,4-triazol-3-one;
    (b) 2-(3-methoxyphenyl)-4-methyl-5-phenyl-3H-1,2,4-triazol-3-one;
    (c) 2-(2-bromophenyl)-4-methyl-5-phenyl-3H-1,2,4-triazol-3-one;
    (d) 5-(4-methoxyphenyl)-4-methyl-2-phenyl-3H-1,2,4-triazol-3-one;
    (e) 5-(2-methoxyphenyl)-4-methyl-2-phenyl-3H-1,2,4-triazol-3-one;
    (f) 4-(2-N,N-dimethylaminoethyl)-2-(2-methylphenyl)-5-phenyl-3H-1,2,4-triazol-3-one;
    (g) 2-(2-methoxyphenyl)-5-phenyl-3H-1,2,4-triazol-3-one;
    (h) 2-(2-chlorophenyl)-5-phenyl-3H-1,2,4-triazol-3-one;
    (i) 2-(3-chlorophenyl)-4-(2-N,N-dimethylaminoethyl)-5-phenyl-3H-1,2,4-triazol-3-one;
    (j) 2-(2-fluorophenyl)-5-phenyl-3H-1,2,4-triazol-3-one;
    (k) 2-(3-fluorophenyl)-4-methyl-5-phenyl-3H-1,2,4-triazol-3-one;
    (l) 2-(2-fluorophenyl)-4-methyl-5-phenyl-3H-1,2,4-triazol-3-one;
    (m) 2-(3-methylphenyl)-5-phenyl-3H-1,2,4-triazol-3-one;
    (n) 2-(2-ethylphenyl)-5-phenyl-3H-1,2,4-triazol-3-one;
    (o) 2-(3-fluorophenyl)-4-(2-N,N-dimethylaminoethyl)-5-phenyl-3H-1,2,4-triazol-3-one;

(p) 4-methyl-2-(3-methylphenyl)-5-phenyl-3H-1,2,4-triazol-3-one;

(q) 4-(2-N,N-dimethylaminoethyl)-2-(3-methylphenyl)-5-phenyl-3H-1,2,4-triazol-3-one;

(r) 2-(2-chlorophenyl)-4-methyl-5-phenyl-3H-1,2,4-triazol-3-one; and (s) 2-(2-bromophenyl)-5-phenyl-3H-1,2,4-triazol-3-one, or pharmaceutically acceptable salts thereof.

2. A pharmaceutical composition comprising a compound selected from the group consisting of:

(a) 2-(2-bromophenyl)-4-methyl-5-phenyl-3H-1,2,4-triazol-3-one;

(b) 5-(2-methoxyphenyl)-4-methyl-2-phenyl-3H-1,2,4-triazol-3-one;

(c) 2-(2-methoxyphenyl)-5-phenyl-3H-1,2,4-triazol-3-one;

(d) 2-(2-chlorophenyl)-5-phenyl-3H-1,2,4-triazol-3-one;

(e) 2-(3-chlorophenyl)-4-(2-N,N-dimethylaminoethyl)-5-phenyl-3H-1,2,4-triazol-3-one;

(f) 2-(2-fluorophenyl)-5-phenyl-3H-1,2,4-triazol-3-one;

(g) 2-(3-fluorophenyl)-4-methyl-5-phenyl-3H-1,2,4-triazol-3-one;

(h) 2-(2-fluorophenyl)-4-methyl-5-phenyl-3H-1,2,4-triazol-3-one;

(i) 2-(3-fluorophenyl)-4-(2-N,N-dimethylaminoethyl)-5-phenyl-3H-1,2,4-triazol-3-one;

(j) 4-methyl-2-(3-methylphenyl)-5-phenyl-3H-1,2,4-triazol-3-one;

(k) 4-(2-N,N-dimethylaminoethyl)-2-(3-methylphenyl)-5-phenyl-3H-1,2,4-triazol-3-one;

(l) 2-(2-chlorophenyl)-4-methyl-5-phenyl-3H-1,2,4-triazol-3-one; and (m) 2-(2-bromophenyl)-5-phenyl-3H-1,2,4-triazol-3-one; or a pharmaceutically acceptable salt thereof.

3. A method of treating a neurodegenerative disease or cerebral ischemia arising from conditions selected from the group consisting of Status epilepticus, hypoglycaemia, hypoxia, anoxia, brain trauma, brain oedema, amyotrophic lateral sclerosis, Huntington's disease, Alzheimer's disease, hypotonia, cardiac infarction, brain pressure (elevated intracranial pressure), ischaemic and haemorrhagic stroke, global cerebral ischaemia with heart stoppage, diabetic polyneuropathy, tinnitus, perinatal asphyxia, psychosis, schizophrenia, depression, and Parkinson's disease, the method of treatment comprising administering to a host in need of such treatment a therapeutic amount of a pharmaceutical composition according to claim 1.

4. A method of treating a neurodegenerative disease or cerebral ischemia arising from conditions selected from the group consisting of Status epilepticus, hypoglycaemia, hypoxia, anoxia, brain trauma, brain oedema, amyotrophic lateral sclerosis, Huntington's disease, Alzheimer's disease, hypotonia, cardiac infarction, brain pressure (elevated intracranial pressure), ischaemic and haemorrhagic stroke, global cerebral ischaemia with heart stoppage, diabetic polyneuropathy, tinnitus, perinatal asphyxia, psychosis, schizophrenia, depression, and Parkinson's disease, the method of treatment comprising administering to a host in need of such treatment a therapeutic amount of a pharmaceutical composition according to claim 2.

* * * * *